United States Patent
Owa et al.

(10) Patent No.: US 7,015,241 B2
(45) Date of Patent: Mar. 21, 2006

(54) APPETITE-STIMULATING AGENTS AND REMEDIES FOR ANOREXIA

(75) Inventors: Takashi Owa, Tsukuba (JP); Yoichi Ozawa, Tsukuba (JP); Takayuki Hida, Tsukuba (JP); Norimasa Miyamoto, Tsukuba (JP); Takeshi Nagasu, Tsuchiura (JP); Tatsuo Okauchi, Kitakyushu (JP); Hiroshi Yoshino, Abiko (JP); Naoko Hata, Tsukuba (JP); Kentaro Yoshimatsu, Tsuchiura (JP); Nozomu Koyanagi, Tsukuba (JP); Kyosuke Kito, Tsukuba (JP)

(73) Assignee: Eisai Co., Ltd., Tokyo (JP)

( * ) Notice: Subject to any disclaimer, the term of this patent is extended or adjusted under 35 U.S.C. 154(b) by 14 days.

(21) Appl. No.: 10/488,825

(22) PCT Filed: Sep. 5, 2002

(86) PCT No.: PCT/JP02/09031

§ 371 (c)(1),
(2), (4) Date: Mar. 5, 2004

(87) PCT Pub. No.: WO03/022272

PCT Pub. Date: Mar. 20, 2003

(65) Prior Publication Data

US 2004/0242628 A1  Dec. 2, 2004

(30) Foreign Application Priority Data

Sep. 5, 2001 (JP) .............................. 2001-269481

(51) Int. Cl.
*A01N 43/38* (2006.01)
(52) U.S. Cl. ..................................... 514/415
(58) Field of Classification Search ................ 514/415
See application file for complete search history.

(56) References Cited

U.S. PATENT DOCUMENTS 5,721,246 A * 2/1998 Yoshino et al. ............. 514/300
6,469,043 B1 10/2002 Haneda et al. ............. 514/414

FOREIGN PATENT DOCUMENTS

| EP | 1 070 705 | 1/2001 |
|---|---|---|
| JP | 08-231505 | 9/1996 |
| JP | 2000-309534 | 11/2000 |
| WO | WO 98/15530 | 4/1998 |
| WO | WO 98/27081 | 6/1998 |

OTHER PUBLICATIONS

See-Lasley, et al, Manual of Oncology Therapeutics, 1981, p. 9.*

* cited by examiner

*Primary Examiner*—Rebecca Cook
(74) *Attorney, Agent, or Firm*—Andrea L.C. Robidoux; Choate, Hall & Stewart LLP

(57) ABSTRACT

An appetite-stimulating agent and a therapeutic agent for anorexia, each comprising, as an active ingredient, a sulfonamide derivative or sulfonic acid ester derivative represented by the following general formula (I):

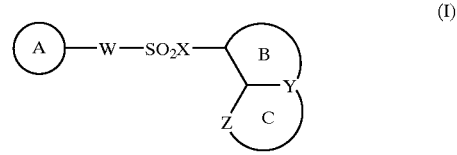

wherein the ring A represents a monocyclic or bicyclic aromatic ring which may be substituted,
the ring B represents a 6-membered unsaturated hydrocarbon ring or a 6-membered unsaturated heterocyclic ring containing one nitrogen atom as a heteroatom, each of which may be substituted,
the ring C represents a 5-membered heterocyclic ring containing one or two nitrogen atoms, which may be substituted,
W represents a single bond or —CH=CH—,
X represents —N($R^1$)— or an oxygen atom,
Y represents a carbon atom or a nitrogen atom,
Z represents —N($R^2$)— or a nitrogen atom, and
$R^1$ and $R^2$ may be identical or different and each represents a hydrogen atom or a lower alkyl group, or a pharmacologically acceptable salt thereof, or a hydrate thereof.

14 Claims, 2 Drawing Sheets

APPETITE-STIMULATING AGENTS AND REMEDIES FOR ANOREXIA

TECHNICAL FIELD

This application is the U.S. National Stage of International Application No. PCT/JP02/09031, filed Sep. 5, 2002, published in Japanese. This application claims priority benefits under 35 U.S.C. § 119 or 365 to Japan Patent Application No. 2001-269481, filed Sep. 5, 2001. The entire teachings of the above applications are incorporated herein by reference.

The present invention relates to an appetite-stimulating agent. The present invention also relates to a therapeutic agent for anorexia, and more particularly to therapeutic agents for anorexia nervosa, apocleisis emaciation, and anorexia and emaciation accompanying cancerous cachexia.

BACKGROUND ART

Appetite and eating behavior are controlled by a network mechanism in which various regulator groups are complexly linked with one another, thereby maintaining a constant internal environment and body weight. However, in recent years, while adiposis is increasing among children and middle-aged and elderly persons, emaciation accompanied with anorexia is increasing mainly among young women. Thus, failure of an eating-control mechanism has been widely recognized as a pathological condition. In particular, anorexia nervosa has been increasing in number year by year, now becoming one of diseases attracting even social attention. This disease is characterized by an extreme fall in the intake amount and uncontrollableness of maintaining a normal weight over the minimum due to the fall. Slightly more than 90% of the patients suffering from the disease are women, and the disease ranks high in the adolescent female mortality rate. Because the disease is caused by an addition of a psychological trauma (pointing out of fatness, etc.) or a stress to a problem in growth or a genetic factor, principal treatment means therefore depend much on hospitalized behavior therapy.

For cancerous cachexia recognized in about 80% of patients dying of cancer, appetite depression and emaciation, which are concomitant symptoms, are the problems when considering a quality of life of a patient suffering from cancer, so that researches have been advanced regarding a mechanism of eating disorders and a treatment strategy more intensively than ever. Although the cause of inappetence accompanied with suffering from cancer has not necessarily been elucidated yet, participation of various substances causing dysbolism (proinflammatory cytokines, neuroendocrine hormones, neurotransmitters, eicosanoids, tumor-derived factors, etc.) has been proposed, based on an idea that "a substance causing cancerous cachexia being equal to a factor inducing appetite depression". The prior treatment is mainly a forced energy supply by transfusion, while it is also known that the condition of cancerous cachexia is not necessarily improved only by the treatment. As recent trends in treatment methods, there is an example in which use of corticosteroids and synthesized progesterons (megestorol acetate or medroxyprogesteron acetate) is recommended to stimulate appetite of a patient suffering from cancer who is recognized as having appetite depression or weight reduction. However, a guideline is still not clearly defined regarding how to use the above for obtaining the maximum effect, analyses of results from future clinical trials are expected. Furthermore, agonists or antagonists of neuropeptides or drugs targeting TNF-α, IL-6, CRP, for example, are developed and are now in a stage of clinical trial thereof [referential literature: Nihon Rinsho, Vol 59, No 3, 515–520 (2001)]. Additionally, because combinational use of anti-cancer drugs is widely adopted in chemotherapies of cancer, it is considered that there is a possibility of treatment with combinational use of existing anticancer drugs, in treatment of appetite depression and emaciation accompanied with cancerous cachexia.

Under such circumstances as above, detailed elucidation of the eating-control mechanism is still being researched, and especially, clinical problems on anorexia and emaciation are not sufficiently solved. Therefore, in addition to the treatment methods currently used, there is a strong desire for development of a further improved method or a novel treatment method.

JP 7-165708 A, JP 8-231505 A, and JP 2000-247949 A disclose the same sulfonamide compounds and sulfonic acid ester compounds as the present invention, but there is no description about the appetite-stimulating effect thereof.

DISCLOSURE OF THE INVENTION

An object of the present invention is to provide an appetite-stimulating agent having an excellent appetite-stimulating effect. Another object of the present invention is to provide a therapeutic agent for anorexia based on an appetite-stimulating effect.

In view of the above, the inventors of the present invention have made intensive studies for seeking an excellent appetite-stimulating agent, and found that a sulfonamide compound and a sulfonic acid ester compound having a bicyclic hetero ring have an excellent appetite-stimulating effect and also have less toxicity, thus completing the present invention.

The present invention provides an appetite-stimulating agent comprising, as an active ingredient, a sulfonamide derivative or sulfonic acid ester derivative represented by the following general formula (I):

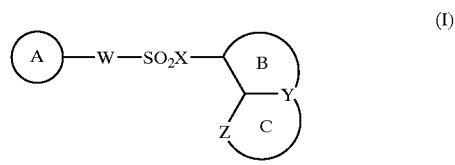

wherein the ring A represents a monocyclic or bicyclic aromatic ring which may be substituted, the ring B represents a 6-membered unsaturated hydrocarbon ring or a 6-membered unsaturated heterocyclic ring containing one nitrogen atom as a heteroatom, each of which may be substituted, the ring C represents a 5-membered heterocyclic ring containing one or two nitrogen atoms, which may be substituted, W represents a single bond or —CH=CH—, X represents —N($R^1$)— or an oxygen atom, Y represents a carbon atom or a nitrogen atom, Z represents —N($R^2$)— or a nitrogen atom, and $R^1$ and $R^2$ may be identical or different and each represents a hydrogen atom or a lower alkyl group, or a pharmacologically acceptable salt thereof, or a hydrate thereof.

The present invention also provides a therapeutic agent for anorexia, comprising, as an active ingredient, a sulfonamide derivative or sulfonic acid ester derivative represented by the above general formula (I), or a pharmacologically acceptable salt thereof, or a hydrate thereof.

In the general formula (I), it is preferred that W is a single bond. More preferably, X and Z are —NH—, and Y is a carbon atom.

In the general formula (I), it is preferred that the ring B is benzene or pyridine, each of which may be substituted.

In the general formula (I), it is preferred that the ring C is pyrrole which may be substituted.

In the general formula (I), it is preferred that the ring A is benzene or pyridine, each of which may be substituted; the ring B is benzene which may be substituted; the ring C is pyrrole which may be substituted; W is a single bond; and X and Z are —NH—.

Examples of the anorexia include anorexia nervosa, apocleisis emaciation, and anorexia and emaciation accompanying cancerous cachexia.

When the anorexia is anorexia and emaciation accompanying cancerous cachexia, it is preferred that the agent further comprises an anticancer drug.

BEST MODE FOR CARRYING OUT THE INVENTION

Figure 1:
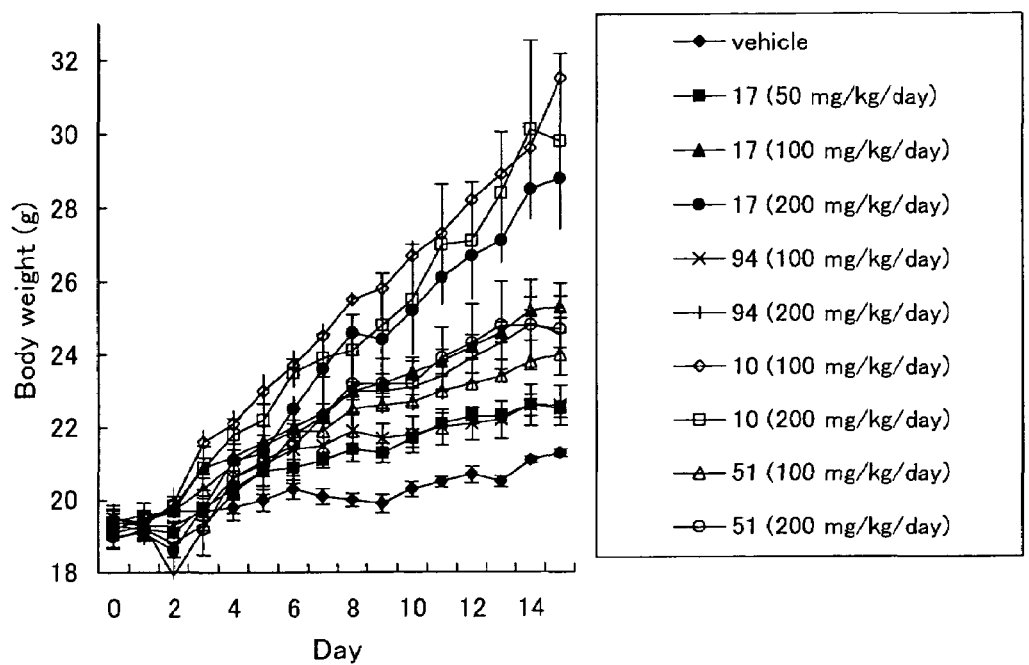
FIG. 1 shows an increase in the body weight of a mouse when the compound used in the present invention is administered to the mouse.

In the general formula (I), the "monocyclic or bicyclic aromatic ring which may be substituted" represented by the ring A is an aromatic hydrocarbon ring or an aromatic heterocyclic ring containing at least one of nitrogen, oxygen and sulfur atoms, each of which may have one to three substituents thereon. Examples of such aromatic rings included in the ring A include pyrrole, pyrazole, imidazole, thiophene, furan, thiazole, oxazole, benzene, pyridine, pyrimidine, pyrazine, pyridazine, naphthalene, quinoline, isoquinoline, phthalazine, naphthyridine, quinoxaline, quinazoline, cinnoline, indole, isoindole, indolizine, indazole, benzofuran, benzothiophene, benzoxazole, benzimidazole, benzopyrazole, benzothiazole and so forth. They may have one to three substituents. When two or more substituents are present, they may be the same or different. Examples of the substituents include an amino group which may be substituted with a lower alkyl group or a lower cycloalkyl group; a lower alkyl group; a lower alkoxy group; hydroxyl; nitro; mercapto; cyano; a lower alkylthio group; a halogen group; a group represented by the formula -a-b wherein a represents a single bond, —(CH$_2$)$_k$—, —O—(CH$_2$)$_k$—, —S—(CH$_2$)$_k$— or —N(R$^3$)—(CH$_2$)$_k$—, k is an integer of 1 to 5, R$^3$ represents a hydrogen atom or a lower alkyl group, and b represents —CH$_2$-d (wherein d represents an amino group which may be substituted with a lower alkyl group, a halogen group, hydroxyl, a lower alkylthio group, cyano or a lower alkoxy group); a group represented by the formula -a-e-f wherein a has the same meaning as defined above, e represents —S(O)— or —S(O)$_2$—, f represents an amino group which may be substituted with a lower alkyl group or a lower alkoxy group, a lower alkyl group, trifluoromethyl, —(CH$_2$)$_m$-b or —N(R$^4$)—(CH$_2$)$_m$-b (wherein b has the same meaning as defined above, R$^4$ represents a hydrogen atom or a lower alkyl group, and m is an integer of 1 to 5); a group represented by the formula -a-g-h wherein a has the same meaning as defined above, g represents —C(O)— or —C(S)—, h represents an amino group which may be substituted with a lower alkyl group, hydroxyl, a lower alkyl group, a lower alkoxy group, —(CH$_2$)$_n$-b or —N(R$^5$)—(CH$_2$)$_n$-b (wherein b has the same meaning as defined above, R$^5$ represents a hydrogen atom or a lower alkyl group, and n is an integer of 1 to 5); a group represented by the formula -a-N(R$^6$)-g-i wherein a and g have the same meanings as defined above, R$^6$ represents a hydrogen atom or a lower alkyl group, i represents a hydrogen atom or a lower alkoxy group or f (f has the same meaning as defined above); a group represented by the formula -a-N(R$^7$)-e-f wherein a, e and f have the same meanings as defined above, and R$^7$ represents a hydrogen atom or a lower alkyl group; a group represented by the formula —(CH$_2$)$_p$-j-(CH$_2$)$_q$-b wherein j represents an oxygen atom or a sulfur atom, b has the same meaning as defined above, and p and q may be the same or different and each represents an integer of 1 to 5; a group represented by the formula —(CH$_2$)$_u$-Ar wherein Ar represents a phenyl group or a heteraryl group, which may be substituted with a lower alkyl group, a lower alkoxy group or a halogen atom and u represents 0 or an interger of 1 to 5; a group represented by the formula —CONH—(CH$_2$)$_u$-Ar wherein Ar and u have the same meaning as defined above; a group represented by the formula —SO$_2$—(CH$_2$)$_u$-Ar wherein Ar and u have the same meaning as defined above; and so forth.

When the substituent is an amino group substituted with two of alkyl groups, both of the alkyl groups may bond to form a 5- or 6-membered ring. Further, when the ring A is a nitrogen-containing heterocyclic ring having hydroxyl or mercapto, these groups may present in the form of an oxo or thioxo group by resonance.

The "6-membered unsaturated hydrocarbon ring or 6-membered unsaturated heterocyclic ring containing one nitrogen atom as a heteroatom, which may be substituted" represented by the ring B means benzene or pyridine which may be partially hydrogenated. It may have one or two of substituents on the ring, and when two of substituents are present, they may be the same or different.

The "5-membered heterocyclic ring containing one or two nitrogen atoms, which may be substituted" represented by the ring C means pyrrole, pyrazole or imidazole which may be partially hydrogenated. It may have one or two of substituents on the ring, and when two of substituents are present, they may be the same or different.

Examples of the substituents that the rings of B and C may have include a halogen group, cyano, a lower alkyl group, a lower alkoxy group, hydroxyl, oxo, a group represented by the formula —C(O)-r (wherein r represents a hydrogen atom, an amino group which may be substituted with a lower alkyl group, a lower alkyl group, a lower alkoxy group or hydroxyl), an amino group substituted with a lower alkyl group, trifluoromethyl and so forth.

In the general formula (I), the lower alkyl group in the definitions of R$^1$ and R$^2$ as well as the substituents that the rings of A, B and C may have means a linear or branched alkyl group having 1 to 6 carbon atoms, and examples thereof include methyl, ethyl, n-propyl, isopropyl, n-butyl, isobutyl, sec-butyl, tert-butyl, n-pentyl (amyl), isopentyl, neopentyl, tert-pentyl, 1-methylbutyl, 2-methylbutyl, 1,2-dimethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and so forth. Among these, methyl, ethyl, n-propyl, isopropyl, n-butyl and isobutyl are preferred, and methyl, ethyl, n-propyl and isopropyl are most preferred.

The lower cycloalkyl group mentioned in the definitions of the substituents that the ring of A may have means a cycloalkyl group having 3 to 8 carbon atoms, and examples thereof include cyclopropyl, cyclopentyl, cyclohexyl and so forth.

The lower alkoxy mentioned in the definitions of the substituents that the rings of A, B and C may have means an alkoxyl group derived from the aforementioned lower alkyl group, such as methoxy, ethoxy, n-propoxy, isopropoxy, n-butoxy, isobutoxy and tert-butoxy. Among these, methoxy and ethoxy are most preferred. The lower alkylthio group means an alkylthio group derived from the aforementioned lower alkyl group. Further, examples of the halogen atom include a fluorine atom, a chlorine atom, a bromine atom and so forth.

The sulfonamide derivatives or the sulfonic acid ester derivatives represented by the general formula (I) may form a salt with an acid or a base. The active ingredient used in the present invention also includes salts of the sulfonamide derivatives or the sulfonic acid ester represented by the general formula (I). Examples of the salt with an acid include salts with inorganic acids, such as hydrochlorides, hydrobromides and sulfates, and salts with organic acids such as acetic acid, lactic acid, succinic acid, fumaric acid, maleic acid, citric acid, benzoic acid, methanesulfonic acid and p-toluenesulfonic acid. Examples of the salt with a base include salts with inorganic bases, such as sodium salts, potassium salts and calcium salts and salts with organic bases such as triethylamine, arginine and lysine.

It is needless to say that the compounds include hydrates and optical isomers of these compounds if they are present.

A list of specific examples of the sulfonamide derivative or the sulfonic acid ester derivative represented by the general formula (I) or the pharmacologically acceptable salt, or the hydrate thereof is as follows:

Compound 1
N-(1H-Indol-7-yl)-4-nitrobenzenesulfonamide

Compound 2
N-(3-Chloro-1H-indol-7-yl)-4-nitrobenzenesulfonamide

Compound 3
4-Amino-N-(3-chloro-1H-indol-7-yl)benzenesulfonamide

Compound 4
N-(3-Chloro-1H-indol-7-yl)-4-(methanesulfonamido)-benzenesulfonamide

Compound 5
4-Bromomethyl-N-(1H-indol-7-yl)benzenesulfonamide

Compound 6
N-(1,3-Dihydro-2H-indol-2-on-7-yl)-4-methyl-benzenesulfonamide

Compound 7
3-Chloro-N-(3-chloro-1H-indol-7-yl)benzenesulfonamide

Compound 8
4-Amino-N-(3,4-dichloro-1H-indol-7-yl)benzenesulfonamide

Compound 9
4-[N-(1H-Indol-7-yl)sulfamoyl]benzoic acid

Compound 10
N-(3-Chloro-1H-indol-7-yl)-4-cyanobenzenesulfonamide

Compound 11
3-Chloro-N-(3-chloro-4-methoxy-1H-indol-7-yl)-benzenesulfonamide

Compound 12
3-Chloro-N-(3-chloro-4-hydroxy-1H-indol-7-yl)-benzenesulfonamide

Compound 13
N-(1H-Indol-7-yl)-4-methoxybenzenesulfonamide

Compound 14
6-Chloro-N-(3-chloro-1H-indol-7-yl)-3-pyridinesulfonamide

Compound 15
N-(3-Chloro-1H-indol-7-yl)-4-(methylthiomethyl)-benzenesulfonamide

Compound 16
3-Chloro-N-(3-formyl-1H-indol-7-yl)benzenesulfonamide

Compound 17
3-Chloro-N-(3-cyano-1H-indol-7-yl)benzenesulfonamide

Compound 18
6-Chloro-N-(3-cyano-1H-indol-7-yl)-3-pyridinesulfonamide

Compound 19
N-(3-Chloro-1H-indol-7-yl)-4-sulfamoylbenzenesulfonamide

Compound 20
3-Chloro-N-(8-imidazo[1,2-a]pyridinyl)benzenesulfonamide hydrochloride Compound 21
N-(3,4-Dichloro-1H-indol-7-yl)-4-sulfamoyl-benzenesulfonamide Compound 22
N-(3-Chloro-1H-indol-7-yl)-4-(methylthio)benzenesulfonamide Compound 23
N-(3-Chloro-1H-indol-7-yl)-4-(methylsulfonyl)-benzenesulfonamide Compound 24
N-(3-Chloro-1H-indol-7-yl)-4-(methylsulfinyl)-benzenesulfonamide Compound 25
3-Chloro-N-(3-chloro-1H-pyrrolo[3,2-c]pyridin-7-yl)-benzenesulfonamide Compound 26
4-Acetamido-N-(3-chloro-4-methyl-1H-indol-7-yl)-benzenesulfonamide Compound 27
4-Amino-N-(3-chloro-4-methyl-1H-indol-7-yl)-benzenesulfonamide Compound 28
4-Cyano-N-(3-chloro-1H-indol-7-yl)benzenesulfonamide Compound 29
4-Carbamoyl-N-(3-chloro-1H-indol-7-yl)benzenesulfonamide Compound 30
N-(4-Bromo-1H-indol-7-yl)-4-nitrobenzenesulfonamide Compound 31
N-(3-Chloro-4-cyano-1H-indol-7-yl)-4-nitro-benzenesulfonamide Compound 32
4-Amino-N-(3-chloro-4-cyano-1H-indol-7-yl)-benzenesulfonamide Compound 33
4-Amino-N-(3-chloro-1H-indol-7-yl)-3-pyridinesulfonamide Compound 34
N-(3-Chloro-1H-indol-7-yl)-4-(methylsulfinylmethyl)-benzenesulfonamide Compound 35
N-(3-Chloro-1H-indol-7-yl)-4-(2-sulfamoylethyl)-benzenesulfonamide Compound 36
N-(3-Chloro-1H-indol-7-yl)-4-[2-(methylsulfonyl)ethyl]-benzenesulfonamide Compound 37
6-Amino-N-(3-cyano-1H-indol-7-yl)-3-pyridinesulfonamide Compound 38
4-Acetamide-3-chloro-N-(3-chloro-1H-indol-7-yl)-benzenesulfonamide Compound 39
N-(3-Cyano-1H-indol-7-yl)-8-quinolinesulfonamide Compound 40
5-Chloro-N-(3-cyano-1H-indol-7-yl)-2-thiophenesulfonamide Compound 41
N-(3-Chloro-1H-indol-7-yl)-4-(methoxycarbonylamino)-benzenesulfonamide Compound 42
4-Acetyl-N-(3-cyano-1H-indol-7-yl)benzenesulfonamide Compound 43
N-(3-Chloro-1H-indol-7-yl)-4-(N-methoxysulfamoyl)-benzenesulfonamide Compound 44
N-(3-Cyano-1H-indol-7-yl)-β-styrenesulfonamide Compound 45
3-Chloro-N-(3-cyano-1H-indol-7-yl)-2-methyl-benzenesulfonamide Compound 46
N-(3-Chloro-1H-indol-7-yl)-6-isopropylamino-3-pyridinesulfonamide Compound 47
N-(3-Chloro-1H-indol-7-yl)-6-[[2-(dimethylamino)-ethyl]amino]-3-pyridinesulfonamide Compound 48
N-(3-Cyano-1H-indol-7-yl)-2-furansulfonamide Compound 49
N-(3-Chloro-1H-indol-7-yl)-4-[(dimethylaminosulfonyl)-amino]benzenesulfonamide Compound 50
N-(3-Methyl-1H-indol-7-yl)-4-(methylsulfonyl)-benzenesulfonamide Compound 51
3-Cyano-N-(3-cyano-1H-indol-7-yl)benzenesulfonamide Compound 52
N-(3-Chloro-1H-indol-7-yl)-4-(N-methylmethanesulfonamido)-benzenesulfonamide Compound 53
N-(3-Chloro-1H-indol-7-yl)-4-[(methanesulfonamido)methyl]-benzenesulfonamide Compound 54
N-(3-Chloro-1H-indol-7-yl)-4-(1-pyrrolidinylsulfonyl)-benzenesulfonamide Compound 55
N-(3-Cyano-1H-indol-7-yl)-1-methyl-4-imidazolesulfonamide Compound 56
N-(3-Chloro-1H-indol-7-yl)-6-[(2-hydroxyethyl)amino]-3-pyridinesulfonamide Compound 57
N-(3-Chloro-1H-indol-7-yl)-6-mercapto-3-pyridinesulfonamide Compound 58
7-(4-Chlorobenzenesulfonamido)-1H-indole-2-carboxylic acid Compound 59
N-(3-Chloro-1H-indol-7-yl)-6-cyclopropylamino-3-pyridinesulfonamide Compound 60
N-(3-Cyano-1H-indol-7-yl)-5-methyl-3-pyridinesulfonamide Compound 61
N-(3-Chloro-1H-indol-7-yl)-4-(N-methylsulfamoyl)-benzenesulfonamide Compound 62
N-(3-Chloro-1H-indol-7-yl)-4-[2-(methanesulfonamido)ethyl]-benzensulfonamide Compound 63
N-(3-Chloro-1H-indol-7-yl)-4-(sulfamoylmethyl)-benzensulfonamide Compound 64
N-(3-Chloro-1H-indol-7-yl)-4-thiocarbamoylbenzensulfonamide Compound 65
5-Bromo-N-(3-cyano-1H-indol-7-yl)-2-pyridinesulfonamide Compound 66
N-(3-Cyano-1H-indol-7-yl)-2-naphthalenesulfonamide Compound 67
N-(3-Acetyl-1H-indol-7-yl)-3-chlorobenzenesulfonamide Compound 68
4-Amino-N-(5-bromo-3-cyano-1H-indol-7-yl)benzenesulfonamide Compound 69
N-(3-Chloro-1H-indol-7-yl)-4-(N-ethylsulfamoyl)-benzenesulfonamide Compound 70
N-(3-Chloro-1H-indol-7-yl)-4-(ethanesulfonamido)-benzenesulfonamide Compound 71
N-(3-Chloro-1H-indol-7-yl)-6-[(2-cyanoethyl)amino]-3-pyridinesulfonamide Compound 72
N-(3-Chloro-1H-indol-7-yl)-4-(N-methylcarbamoyl)-benzenesulfonamide Compound 73
N-(3-Chloro-1H-indol-7-yl)-4-(methylsulfonylmethyl)-benzenesulfonamide Compound 74
N-(3-Chloro-1H-indol-7-yl)-4-(N,N-dimethylsulfamoyl)-benzenesulfonamide Compound 75
N-(3-Chloro-1H-indol-7-yl)-4-(1-pyrrolidinylcarbonyl)-benzenesulfonamide Compound 76
3-Chloro-N-(3-chloro-1H-indol-7-yl)-N-methyl-benzenesulfonamide Compound 77
N-(3,4-Dichloro-1H-indol-7-yl)-4-(sulfamoylmethyl)-benzenesulfonamide Compound 78
N-(3-Cyano-1H-indol-7-yl)-4-[2-(methylsulfonyl)ethyl]-benzenesulfonamide Compound 79
N-(3-Chloro-1H-indol-7-yl)-4-(N-methylacetamido)-benzenesulfonamide Compound 80
N-(3-Chloro-1H-indol-7-yl)-6-hydroxy-3-pyridinesulfonamide Compound 81
N-(3-Chloro-1H-indol-7-yl)-4-[2-(N-methylmethane-sulfonamido)ethyl]benzenesulfonamide Compound 82
N-(3-Chloro-1H-indol-7-yl)-4-(trifluoromethane-sulfonamido)benzenesulfonamide Compound 83
N-(3-Chloro-1H-indol-7-yl)-4-[(N-methylmethane-sulfonamido)methyl]benzenesulfonamide Compound 84
3-Chloro-N-(3-chloro-1H-pyrrolo[2,3-c]pyridin-7-yl)-benzenesulfonamide Compound 85
4-(3-Bromopropyl)-N-(3-chloro-1H-indol-7-yl)-benzenesulfonamide Compound 86
4-[N-(2-Bromoethyl)sulfamoyl]-N-(3-chloro-1H-indol-7-yl)-benzenesulfonamide Compound 87
N-(3-Chloro-1H-indol-7-yl)-4-[3-(1-imidazolyl)propyl]-benzenesulfonamide Compound 88
N-(3-Chloro-1H-indol-7-yl)-4-[N-(2-(2-pyridinyl)ethyl)-carbamoyl]benzenesulfonamide Compound 89
4-Amidino-N-(3-chloro-1H-indol-7-yl)benzenesulfonamide Compound 90
N-(3-Chloro-1H-indol-7-yl)-4-[N-[2-(1-imidazolyl)ethyl]-sulfamoyl]benzenesulfonamide Compound 91
3-(5-Bromonicotinamido)-N-(3-cyano-1H-indol-7-yl)-benzenesulfonamide Compound 92
N-(3-Chloro-1H-indol-7-yl)-4-[N-(2-thiazolyl)sulfamoyl]-benzenesulfonamide Compound 93
5-Chloro-N-(3-chloro-1H-indol-7-yl)-4-(5-methyl-3-pyridinesulfonamido)-2-thiophenesulfonami Compound 94
3-Cyano-N-(3-cyano-4-methyl-1H-indol-7-yl)-benzenesulfonamide The sulfonamide derivative or the sulfonic acid ester derivative represented by the general formula (I), a pharmacologically acceptable salt thereof, or a hydrate of the same (hereinafter, also referred as "the compound represented by the general formula (I)") may be manufactured by various methods. Among them, representative methods are described in JP 07-165708 A, JP 08-231505 A, and JP 2000-247949 A.

The compound represented by the general formula (I) has an excellent appetite-stimulating effect. Thus, the compound represented by the general formula (I) may be used as an active ingredient for an appetite-stimulating agent. It may also be used as an active ingredient of a therapeutic agent for diseases in which appetite stimulation is effective to treatment thereof. Thus, according to the present invention, there is provided a method for stimulating appetite, comprising administering an effective amount of the compound represented by the general formula (I); and a method for treating a disease in which appetite stimulation is effective to treatment thereof, comprising administering an effective amount of the compound represented by the general formula (I). Also, according to the present invention, there is provided a use of the compound represented by the general formula (I) in manufacture of an appetite-stimulating agent, and a use of the compound represented by the general formula (I) in manufacture of a therapeutic agent for a disease in which appetite stimulation is effective to treatment thereof.

The phrase "the compound represented by the general formula (I) as an active ingredient" includes a compound that generates the compound represented by the general formula (I) due to in vivo metabolism such as oxidation, reduction, and hydrolysis.

Similarly, the phrases "administering the compound represented by the general formula (I)" and "use of the compound represented by the general formula (I)" in the present invention also include administering and using a compound which generates the compound represented by the general formula (I) due to in vivo metabolism such as oxidation, reduction, and hydrolysis, respectively.

In the present invention, the word "treatment" also includes alleviating a symptom of a disease.

Examples of the disease in which appetite stimulation is effective to treatment thereof include anorexias. Examples of the anorexias include anorexia nervosa, apocleisis emaciation, anorexia and emaciation accompanying cancerous cachexia, etc.

The compound represented by the general formula (I) may be used in a preparation made by a general method. For example, it may be a composition with a carrier (if used for a medicine, a pharmacologically acceptable carrier).

The compound represented by the general formula (I), if used as a medicine, is administered orally or parenterally. The dose is different depending on degree of a symptom, age of a patient, sex, body weight, sensibility difference, administration method, administration timing, administration interval, medicinal characteristics, preparation, allegation, type, type of active ingredient, or the like. The dose is generally 10 to 6,000 mg, preferably about 50 to 4,000 mg, more preferably 100 to 3,000 mg per day for an adult, which was separately administered generally 1 to 3 time(s) in a day, but there is no particular limitation thereto.

In order to prepare an oral solid dosage form, a vehicle and optionally with a binder, disintegrator, lubricant, colorant, corrective, etc. are added to a base, and a mixture thereof is then treated in accordance with a conventional method to form tablets, coated tablets, granules, fine granules, powder, capsules, etc.

Examples of the vehicle include lactose, cornstarch, saccharose, glucose, sorbitol, crystalline cellulose, and silicon dioxide. Examples of the binder include polyvinyl alcohol, ethylcellulose, methylcellulose, acacia gum, hydroxypropylcellulose, and hydroxypropylmethylcellulose. Examples of the lubricant include magnesium stearate, talc, and silica. As the colorant, one permitted to add to a drug is used. Examples of the corrective include cocoa powder, menthol, aromatic acid, peppermint oil, borneol, and cinnamon powder. As a matter of course, those tablets and granules may optionally be coated appropriately with sugar, gelatin, etc.

In order to prepare an injection, a pH regulator, a buffer, a suspending agent, a solubilizer, a stabilizer, an isotonizing agent, a preservative, etc. are optionally added to a base, and a mixture thereof is then treated in accordance with a conventional method to form an injection for intravenous, hypodermic, or intramuscular injection. The injection may optionally be treated in accordance with a conventional method to form a freeze-dry product.

Examples of the suspending agent include methylcellulose, polysorbate 80, hydroxyethylcellulose, acacia gum, tragacanth powder, sodium carboxymethylcellulose, and polyoxyethylenesorbitan monolaurate.

Examples of the solubilizing agent include polyoxyethylene hardened castor oil, polysorbate 80, nicotinic acid amide, polyoxyethylenesorbitan monolaurate, macrogol, and castor oil fatty acid ethyl ester.

Examples of the stabilizer include sodium sulfite and sodium metasulfite. Examples of the preservative include methyl paraoxybenzoate, ethyl paraoxybenzoate, sorbic acid, phenol, cresol, and chlorocresol.

If the anorexia is anorexia and emaciation accompanying cancerous cachexia, the therapeutic agent for anorexia is preferred to further include an anticancer drug.

Examples of the anticancer drug include 5-fluorouracil, cisplatin, irinotecan hydrochloride, paclitaxel, epirubicin, etc.

The compound represented by the general formula (I) and the anticancer drug may be mixed or separately encased to be packed in a unit.

The compound represented by the general formula (I) and the anticancer drug may be administered simultaneously or in order.

EXAMPLES

The effect of the compounds used in the present invention will now be described with reference to pharmacological experimental examples.

Pharmological Experimental Example 1

Appetite-Stimulating and Body Weight-Increasing Effects

Figure 2:
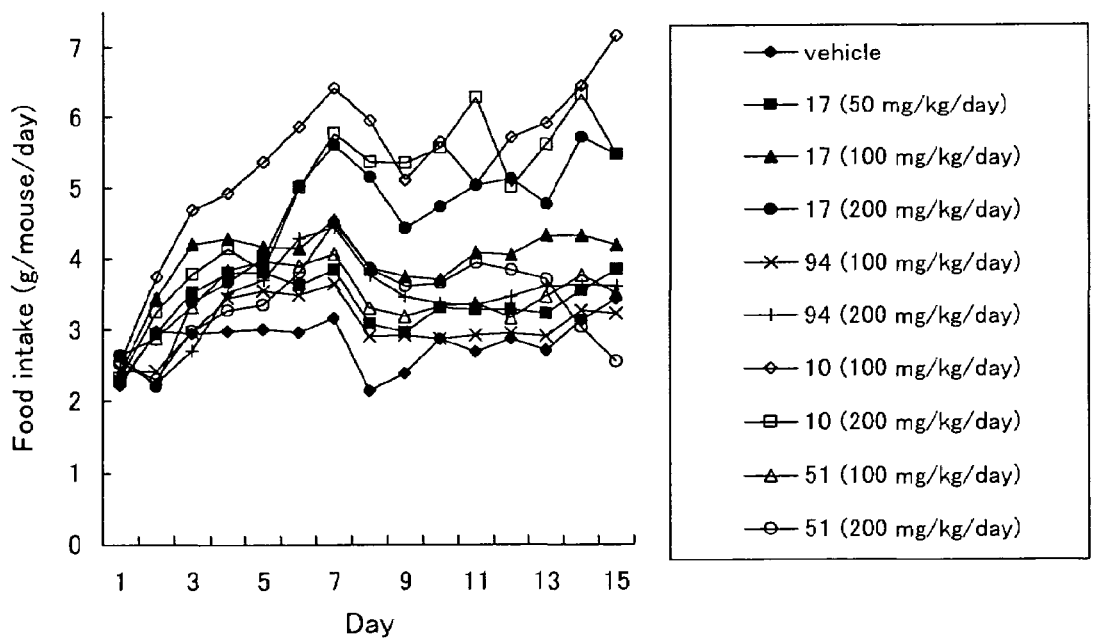
FIG. 2 shows a change of the food consumption of a mouse when the compound used in the present invention is administered to the mouse.

A subjective compound was suspended in saline containing 3.5% dimethylsulfoxide and 6.5% Tween 80, and intraperitoneally administered to $BDF_1$ mice (7 weeks old, female) in a given amount once a day for 15 days (day 0 to day 14). To mice of a control group, saline containing 3.5% dimethylsulfoxide and 6.5% Tween 80 was intraperitoneally administered. Administration was conducted at 1 p.m. every day, and the body weight (day 0 to day 15) and the food intake since the preceding day (day 1 to day 15) were weighed immediately before the administration. The experiments were conducted using 5 mice per group for each of the drug-administered group and the control group. Experimental results for the Compounds 10, 17, 51, and 94 are shown in FIGS. 1 and 2. The numbers of the compound examples are the same as in the list described above (hereinafter, the same applies). As is apparent from the experimental results, it was found that administration of the compounds of the Compounds 10, 17, 51, and 94 increased the body weight and food intake.

Pharmacological Experimental Example 2

Gene Expression Analysis of White Adipose Tissues by GeneChip (Affymetrix)

Figure 3:
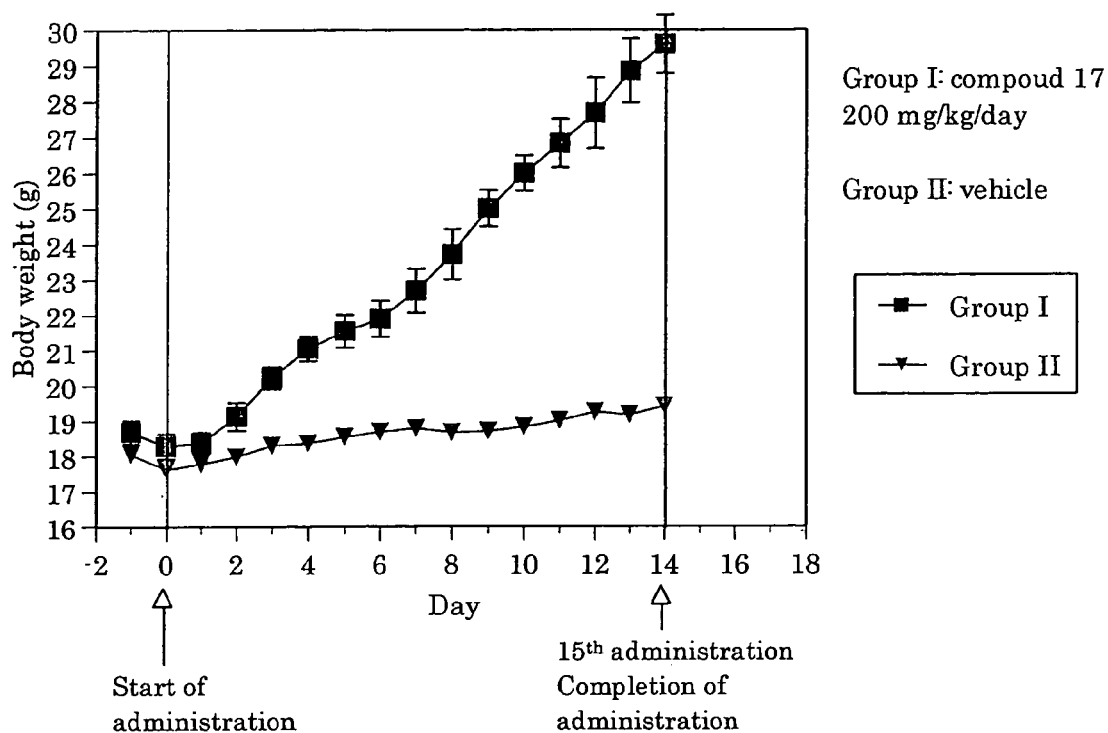
FIG. 3 shows an increase in the body weight of a mouse when the compound of Compound 17 is administered to the mouse.
Figure 4:
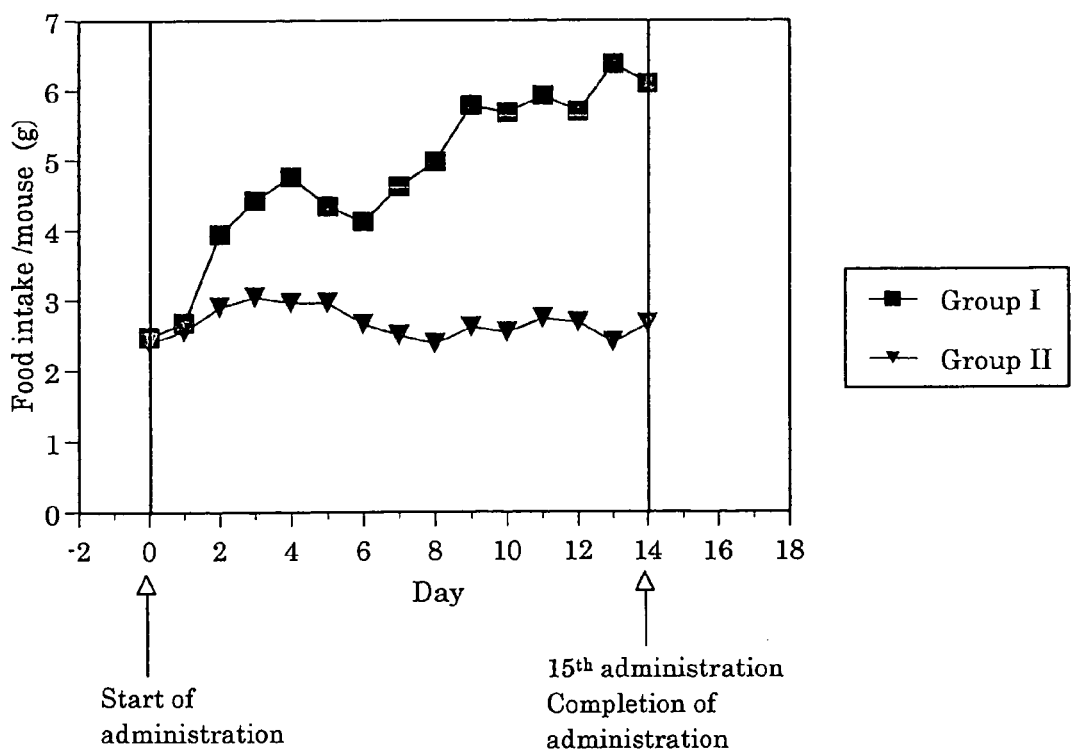
FIG. 4 shows a change of in the food consumption of a mouse when the compound of Compound 17 is administered to the mouse.

The compound of the Compound 17 was suspended in saline containing 3.5% dimethylsulfoxide and 6.5% Tween 80, and intraperitoneally administered to $BDF_1$ mice (7 weeks old, female) in an amount of 200 mg/kg once a day for 15 days (day 0 to day 14). To mice of a control group, saline containing 3.5% dimethylsulfoxide and 6.5% Tween 80 was intraperitoneally administered. The experiments were conducted using 5 mice per group for each of the drug-administered group and the control group. On day 15, white adipose tissues were collected from the mice of the drug-administered group and the control group, and were examined for expression levels of mRNA using GeneChip (Affymetrix) Murine Genome U74A. The experimental operation was conducted in accordance with GeneChip Expression Analysis Technical Manual, and the quantitative analysis was conducted using GeneChip Software. FIG. 3 shows changes in body weights and food intakes of the mice of the drug-administered group and the control group during the experimental period. The comparison results of gene expression patterns of the drug-administered group and the control group elucidated that mRNA levels of a plurality of gene products, which are reported as factors participating in appetite repression or mediators of cancerous cachexia, were significantly repressed. Results regarding representative genes are summarized in Table 1.

TABLE 1

| Accession # | Gene name | Expression level ratio (drug-administered group/control group) |
|---|---|---|
| X54542 | Interleukin-6 | 24% |
| M15131 | Interleukin-1-beta | 22% |
| M88242 | griPGHS* | 26% |

*Glucocorticoid-regulated inflammatory prostaglandin G/H synthase

As is apparent from the above experimental examples, the compound represented by the general formula (I) has an excellent appetite-stimulating effect. Therefore, the compound is useful, as a therapeutic agent for anorexia, in treatment for diseases such as anorexia nervosa, apocleisis emaciation, and anorexia and emaciation accompanying cancerous cachexia.

When the compounds of the Compounds 10, 17, 51, and 94 were administered to mice in a dose of 100 mg/kg and 200 mg/kg successively for 15 days, the mice were in a quite normal condition, with a body weight increase depending on dose, and there was no observation indicating toxicity. Thus, it is considered that the compound represented by the general formula (I) has low toxicity.

INDUSTRIAL APPLICABILITY

An appetite-stimulating agent and a therapeutic agent for anorexia are provided.

What is claimed is:

1. A method for stimulating appetite, comprising administering to a subject in need of appetite stimulation, an effective amount of a sulfonamide derivative or sulfonic acid ester derivative represented by formula (I):

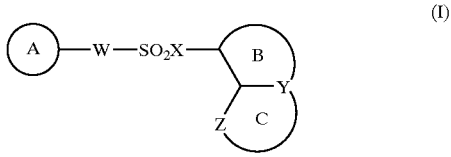

or a pharmacologically acceptable salt thereof, or a hydrate thereof, wherein ring A represents a monocyclic or bicyclic aromatic ring which is optionally substituted, ring B represents a 6-membered unsaturated hydrocarbon ring or a 6-membered unsaturated heterocyclic ring containing one nitrogen atom as a heteroatom, wherein the hydrocarbon ring or the heterocyclic ring is optionally substituted, ring C represents a 5-membered heterocyclic ring containing one or two nitrogen atoms, wherein ring C is optionally substituted, W represents a single bond or —CH=CH—, X represents —N($R^1$)— or an oxygen atom, Y represents a carbon atom or a nitrogen atom, Z represents —N($R^2$)— or a nitrogen atom, and $R^1$ and $R^2$ may be identical or different and each represents a hydrogen atom or a lower alkyl group.

2. The method according to claim 1, wherein W is a single bond.

3. The method according to claim 2, wherein X and Z are —NH—, and Y is a carbon atom.

4. The method according to claim 1, wherein ring B is benzene or pyridine, wherein the benzene or the pyridine is optionally substituted.

5. The method according to claim 1, wherein ring C is pyrrole which is optionally substituted.

6. The method according to claim 1, wherein ring A is benzene or pyridine, wherein the benzene or the pyridine is optionally substituted; ring B is benzene which is optionally substituted; ring C is pyrrole which is optionally substituted; W is a single bond; and X and Z are —NH—.

7. A method of treating anorexia, comprising administering to a mammal in need of treatment of anorexia, an effective amount of a sulfonamide derivative or sulfonic acid ester derivative represented by formula (I):

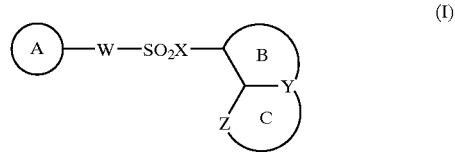

or a pharmacologically acceptable salt thereof, or a hydrate thereof, wherein ring A represents a monocyclic or bicyclic aromatic ring which is optionally substituted, ring B represents a 6-membered unsaturated hydrocarbon ring or a 6-membered unsaturated heterocyclic ring containing one nitrogen atom as a heteroatom, wherein the hydrocarbon ring or the heterocyclic ring is optionally substituted, ring C represents a 5-membered heterocyclic ring containing one or two nitrogen atoms, wherein ring C is optionally substituted, W represents a single bond or —CH=CH—, X represents —N($R^1$)— or an oxygen atom, Y represents a carbon atom or a nitrogen atom, Z represents —N($R^2$)— or a nitrogen atom, and $R^1$ and $R^2$ may be identical or different and each represents a hydrogen atom or a lower alkyl group.

8. The method according to claim 7, wherein W is a single bond.

9. The method according to claim 8, wherein X and Z are —NH—, and Y is a carbon atom.

10. The method according to claim 7, wherein ring B is benzene or pyridine, wherein the benzene or the pyridine is optionally substituted.

11. The method according to claim 7, wherein ring C is pyrrole which is optionally substituted.

12. The method according to claim 7, wherein ring A is benzene or pyridine, wherein the benzene or the pyridine is optionally substituted; ring B is benzene which is optionally substituted; ring C is pyrrole which is optionally substituted; W is a single bond; and X and Z are —NH—.

13. The method according to claim 7, wherein the anorexia is a disease selected from the group consisting of anorexia nervosa, apocleisis emaciation, and anorexia and emaciation accompanying cancerous cachexia.

14. The method according to claim 13, wherein the anorexia is anorexia and emaciation accompanying cancerous cachexia, and the method further comprises administering to the mammal an anticancer drug.

* * * * *